US008703950B2

(12) United States Patent
Keskeny et al.

(10) Patent No.: US 8,703,950 B2
(45) Date of Patent: Apr. 22, 2014

(54) LOW ABUK OXYCODONE, ITS SALTS AND METHODS OF MAKING SAME

(75) Inventors: Erno M. Keskeny, Wilmington, DE (US); James J. Mencel, North Wales, PA (US); Jen-Sen Dung, Boothwyn, PA (US)

(73) Assignee: Johnson Matthey Public Limited Co., London (GB)

( * ) Notice: Subject to any disclaimer, the term of this patent is extended or adjusted under 35 U.S.C. 154(b) by 0 days.

(21) Appl. No.: 13/175,537

(22) Filed: Jul. 1, 2011

(65) Prior Publication Data

US 2012/0259118 A1    Oct. 11, 2012

Related U.S. Application Data

(60) Provisional application No. 61/361,151, filed on Jul. 2, 2010.

(51) Int. Cl.
*C07D 489/02*    (2006.01)
*C07D 489/04*    (2006.01)
*C07D 489/08*    (2006.01)

(52) U.S. Cl.
USPC .................. 546/45; 546/44; 546/46; 514/282

(58) Field of Classification Search
USPC .................. 546/45, 44, 46; 514/282, 280
See application file for complete search history.

(56) References Cited

U.S. PATENT DOCUMENTS

| | | | |
|---|---|---|---|
| 5,847,142 A | 12/1998 | Mudryk et al. |
| 5,869,669 A | 2/1999 | Huang et al. |
| 6,008,355 A | 12/1999 | Huang et al. |
| 6,067,749 A | 5/2000 | Fist et al. |
| 6,090,943 A | 7/2000 | Mudryk et al. |
| 6,177,567 B1 | 1/2001 | Chiu et al. |
| 6,262,266 B1 | 7/2001 | Chiu et al. |
| 6,403,798 B2 | 6/2002 | Chiu et al. |
| 6,864,370 B1 | 3/2005 | Lin et al. |
| 7,071,336 B2 | 7/2006 | Francis et al. |
| 7,129,248 B2 | 10/2006 | Chapman |
| 7,153,966 B2 | 12/2006 | Casner |
| 7,321,038 B2 | 1/2008 | Wang |
| 7,323,565 B2 | 1/2008 | Wang |
| 7,674,799 B2 | 3/2010 | Chapman et al. |
| 7,674,800 B2 | 3/2010 | Chapman |
| 7,683,072 B2 | 3/2010 | Chapman |
| 7,875,623 B2 | 1/2011 | Shafer et al. |
| 7,906,647 B2 | 3/2011 | Cox et al. |
| 2005/0038251 A1 | 2/2005 | Francis et al. |
| 2005/0124811 A1 | 6/2005 | Wang |
| 2005/0222188 A1 | 10/2005 | Chapman et al. |
| 2006/0111383 A1 | 5/2006 | Casner |
| 2006/0173029 A1 | 8/2006 | Chapman et al. |
| 2007/0149559 A1 | 6/2007 | Shafer |
| 2008/0132703 A1 | 6/2008 | Cox et al. |
| 2010/0048905 A1 | 2/2010 | Wang et al. |
| 2010/0152449 A1 | 6/2010 | Chapman et al. |
| 2012/0059167 A1 | 3/2012 | Buehler et al. |

FOREIGN PATENT DOCUMENTS

| | | |
|---|---|---|
| DE | 296916 | 4/1916 |
| EP | 0 889 045 A1 | 1/1999 |
| ES | 2 121 554 A1 | 11/1998 |
| WO | WO-2004/016618 A1 | 2/2004 |
| WO | WO-2004/050025 A2 | 6/2004 |
| WO | 2006019364 | 2/2006 |
| WO | 2006138020 | 12/2006 |
| WO | 2007062184 | 5/2007 |
| WO | 2007103105 | 9/2007 |
| WO | 2008070656 | 6/2008 |
| WO | 2008070658 | 6/2008 |

OTHER PUBLICATIONS

Hiroya et al. Angew. Chem. Int. Ed. Eng. 1995, 34 (20), 2287-2289.*
Ward et al. Can. J. Chem. 1989, 67, 1206-1211.*
Findlay et al., "The Acid-catalyzed Conversion of Codeinone to 8-Hydroxydihydrocodeinone," *J. Am. Chem. Soc.*, 1951, vol. 73, No. 8, pp. 4001-4004.
Proksa, "Separation of Products of Thebaine Rearrangement by Capillary Electrophoresis in the Presence of Cyclodextrins," *Chem. Pap.*, 2001, vol. 55, No. 3, pp. 196-201.
Tada et al., "Ketalisation of α,β-unsaturated ketones. Part I 3-methoxy-N-methylmorphinan derivatives and 14-hydroxycodeinone," *Tetrahedron Letters*, 1969, vol. 10, No. 22, pp. 1805-1808.
Proksa, "10-Hydroxythebaine," Arch. Pharm. Pharm. Med. Chem., 332, pp. 369-370 (1999).
Weiss, J., "Derivatives of Morphine, II. Demethylation of 14-Hydroxycodeinone, 14-Hydroxymorphinone and 8,14-Dihydroxydihydromorphinone," Org. Chem., 22 (11): 1505-08 pp. 1505-1508, (Nov. 1957).
Rapoport et al., "The Synthesis of Thebaine and Northebaine from Codeinone Dimethyl Ketal," Journal of the American Chemical Society, 89:8, 1967, pp. 1942-1947.
Currie et al., "Some Reactions of 14-Hydroxycodeine," Journal of the Chemical Society, Jan. 1, 1960, pp. 773-781, XP008035133.
International Search Report for PCT/US2011/042834 dated Aug. 24, 2011.
Declaration of Steven W. Baldwin, Ph.D. dated Nov. 2, 2009 filed in U.S. Appl. No. 11/729,741, along with Exhibits 1-6.
Roland Kraβnig et al., "Optimization of the Synthesis of Oxycodone and 5-Methyloxycodone," *Arch. Pharm. Pharm. Med. Chem.*, vol. 329, 1996, pp. 325-326.
L. G. Wade, Jr., *Organic Chemistry*, Chapter 7: Reactions of Alkenes (Princeton Hall, Inc., Englewood Cliffs, New Jersey, 1987), pp. 278-332.
Jerry March, *Advanced Organic Chemistry: Reactions, Mechanisms, and Structure*, Fourth Edition (John Wiley & Sons, Inc., 1992), pp. 771-780 and 910-918.

(Continued)

*Primary Examiner* — Sreeni Padmanabhan
*Assistant Examiner* — Irina Neagu
(74) *Attorney, Agent, or Firm* — RatnerPrestia

(57) ABSTRACT

A method of preparing oxycodone includes forming 14-hydroxycodeine by reduction of 14-hydroxycodeinone and rearrangement of the 14-hydroxycodeine to form the oxycodone. During the reduction step, the ketone group of an undesirable contaminant precursor, 8,14-dihydroxy-7,8-dihydrocodeinone, is reduced to a hydroxyl group thus forming a triol. This triol is substantially inert with respect to reforming 14-hydroxycodeinone and can be readily separated from oxycodone.

60 Claims, 5 Drawing Sheets

(56) References Cited

OTHER PUBLICATIONS

G. Marc Loudon, *Organic Chemistry*, Second Edition, Chapter 19.8 (Benjamin/Cummings Publishing Company, Inc., 1988), pp. 780-784.

Robert E. Lutz et al., "Reduction Studies in the Morphine Series: IX. Hydroxycodeinone," *Journal of Organic Chemistry*, vol. 4, No. 3, 1939, pp. 220-233.

Lewis J. Sargent et al., "Hydroxylated Codeine Derivatives," *Journal of Organic Chemistry*, vol. 23, No. 9, pp. 1247-1251, 1958.

F. Vieböck, "Oxydation des Thebains mit Manganiacetat," (Aus d. Pharmzeut.-chem. Universitäts-Laborat. Wien.) (Eingegangen am 28 Dezember 1933.), pp. 197-202.

D. Henschler et al. Structure-Activity Relationships of α,β-Unsaturated Carbonylic Compounds, *The Role of Cyclic Nucleic Acid Adducts in Carcinogenesis and Mutagenisis* (IARC Scientific Publications No. 70—International Agency for Research on Cancer, Lyon, 1986), pp. 197-205.

Iijima et al., "The Oxidation of Thebaine with *m*-Chloroperbenzoic Acid. Studies in the (+)-Morphinan Serices. III$^1$)$^2$)," *Helvetica Chimica Acta*, vol. 60, Fasc. 7 (1977), Nr. 213, pp. 2135-2137.

*Remington's Pharmaceutical Sciences*, Fifth Edition (Mack Publishing Company, Easton, Pennsylvania, 1975), p. 1041.

Iijima et al., Studies in the (+)-Morphinan Series. Synthesis and Biological Properties of (+)-Nalaxone, *Journal of Medicinal Chemistry*, 1978, vol. 21, No. 4, pp. 398-400.

Renzi, Jr. et al., "Quantitative GLC Determination of Oxycodone in Human Plasma," *Journal of Pharmaceutical Sciences*, vol. 68, No. 1, Jan. 1979, pp. 43-45.

\* cited by examiner

LOW ABUK OXYCODONE, ITS SALTS AND METHODS OF MAKING SAME

CROSS-REFERENCE TO RELATED APPLICATIONS

This application claims priority of U.S. Provisional Patent Application No. 61/361,151, filed Jul. 2, 2010, the disclosure of which is incorporated herein by reference in its entirety for all purposes.

BACKGROUND OF THE INVENTION

Various reports have identified the role of two isomers of 8,14-dihydroxy-7,8-dihydrocodeinone in the formation of 14-hydroxycodeinone—an α,β-unsaturated ketone ("ABUK") and a purportedly genotoxic impurity in oxycodone hydrochloride. For example, U.S. Pat. No. 7,683,072 of Chapman et al. notes that "[d]uring salt formation reactions known in the art, the 8,14-dihydroxy-7,8-dihydrocodeinone component is converted to 14-hydroxycodeinone by acid-catalyzed dehydration. See also Weiss, J. Org. Chem., 22(11): 1505-08 (1957). Thus, 14-hydroxycodeinone is increased in the final product." (col. 8, lines 7-12). Similarly, Cox (WO 2008/070656 and WO 2008/070658) notes that "DHDHC [8,14-dihydroxy-7,8-dihydrocodeinone] is easily converted to 14-hydroxycodeinone. This conversion occurs during the conversion of oxycodone base (a.k.a. oxycodone free base) to oxycodone hydrochloride, thus 14-hydroxycodeinone is present in the final oxycodone hydrochloride." (p. 3, lines 5-7). Thus, the isomeric 8,14-dihydroxy-7,8-dihydrocodeinone diols are understood to be unstable such that, during conversion of the oxycodone free base to oxycodone hydrochloride, they undergo acid-catalyzed dehydration to form the 14-hydroxycodeinone ABUK impurity. Weiss teaches that 8,14-dihydroxy-7,8-dihydrocodeinone can be recrystallized from hot 2N HCl if the treatment is rapid, but also reports that treatment in "dilute acid (1:1) in a boiling water bath for 20 minutes" converts the dihydroxy species to 14-hydroxycodeinone. While Weiss does not indicate the mixture of dihydroxy isomers handled during the 2N recrystallization and subsequent hydrolysis to 14-hydroxycodeinone, it implies that both isomers of 8,14-dihydroxy-7,8-dihydrocodeinone will dehydrate to form 14-hydroxycodeinone. Recent reports, including the Chapman '072 patent, and Baldwin (see Baldwin Declaration in support of U.S. patent application Ser. No. 11/729,741) have pointed to the alpha isomer as the apparent more hydrolytically unstable diol of 8,14-dihydroxy-7,8-dihydrocodeinone. Baldwin cites Example 3 of Chapman's U.S. Pat. No. 7,674,800 as demonstrating that dehydration occurs under conditions of aqueous HCl as low as 0.2N at 75° C. Baldwin contrasts this with the Weiss report to assert that one of the two isomers is much more prone to acid catalyzed dehydration.

The present inventors prepared and characterized the 8β,14-dihydroxy-7,8-dihydrocodeinone and used this to develop analytical methodology to measure the alpha and beta isomers by LC/MS to a detection limit of 2 ppm. Two HPLC peaks at relative retention times (RRT) 0.82 and 0.91 versus oxycodone were observed as having a mass corresponding to 8,14-dihydroxy-7,8-dihydrocodeinone upon LC/MS analysis. The peak at RRT 0.91 was identified as the 8β diol. Exposure of a mixture of the two species to acid showed a correlation between the loss of the RRT 0.82 peak with the growth of 14-hydroxycodeinone over a 20 hour period. The peak at RRT 0.91 degraded little under the same conditions over the 20 hour period. On the basis of this study and in view of Baldwin's assertions, the peak at RRT 0.82 was assigned as the 8α diol for the purposes of developing the invention.

A variety of approaches to producing oxycodone hydrochloride with low levels of 14-hydroxycodeinone have been published. The Chapman '072 patent, as well as other patents in the Chapman patent family, and U.S. Patent Application Publication No. 2007/0149559 to Shafer et al., for example, report methods wherein the diols, as contaminants in oxycodone, are dehydrated using aqueous acid or organic acids in organic solvents to form 14-hydroxycodeinone. Chapman describes converting the 14-hydroxycodeinone to oxycodone by hydrogenation as the dehydration occurs. This prevents reversal by rehydration of the 7,8 double bond and minimizes the possibility of having 8,14-dihydroxy-7,8-dihydrocodeinone as an ABUK precursor in the final oxycodone hydrochloride product. Shafer traps the 14-hydroxycodeinone with a thiol nucleophile, forming a water-extractable adduct that can be readily separated from oxycodone.

International Patent Application Publication No. WO 2007/103105 of Buehler et al. likewise describes conditions that may dehydrate the diols to an extent and, in a fashion similar to Shafer, treats the 14-hydroxycodeinone with a sulfur nucleophile or a sulfur-containing inorganic acid or salt thereof to form a water-soluble adduct. The Buehler procedure uses species akin to meta-bisulfite, which react with oxycodone in a 1,2 fashion and with 14-hydroxycodeinone in a 1,4 and 1,2 fashion to form soluble adducts of each. Upon a pH adjustment to ca. pH 9, the 1,2 sulfite adducts hydrolyze to the ketone; however, the 1,4 adduct derived from 14-hydroxycodeinone remains intact and confers water solubility. At pH 9, the oxycodone precipitates or may be preferentially extracted into organic solvent and the adducted 14-hydroxycodeinone remains in the aqueous mixture. The Shafer approach differs in emphasizing the formation of the 1,4 adduct of 14-hydroxycodeinone and does not explicitly rely upon selective 1,2 hydrolysis to recover and separate the oxycodone from the water-soluble 1,4 adduct.

The derivatization of 14-hydroxycodeinone with a sulfur-based reagent, either as a free species or resin-bound, is common to Shafer, Cox and Buehler. At least Chapman and Shafer find commonality in: (1) forcing the dehydration of the diols in the presence of oxycodone; and (2) subsequently consuming or removing the resulting 14-hydroxycodeinone either as oxycodone or as a derivative separable from oxycodone.

SUMMARY OF THE INVENTION

The inventors have found that the alpha diol of 8,14-dihydroxy-7,8-dihydrocodeinone can be present in up to 1,000 ppm in oxycodone base, and that the beta diol can be present at even higher levels. In essence, the approaches outlined above have the potential to actively create and contaminate oxycodone hydrochloride with over 1,000 ppm of the undesired, purportedly genotoxic, impurity then require measures to rigorously remove the impurity. There is also the chance that measures to destroy diol precursors may not proceed exhaustively as noted, for example, in Example 3 of U.S. Pat.

No. 7,129,248 of Chapman et al., where a cautionary note appears that purified oxycodone salt must be handled with care to avoid dehydrating remaining diols to reform 14-hydroxycodeinone and contaminate the product.

The above approaches include the conversion of the diols to 14-hydroxycodeinone in the presence of oxycodone free base. A variety of chemical approaches are used to remove the 14-hydroxycodeinone, especially during conversion of the oxycodone free base to oxycodone hydrochloride. Thus, the above approaches include the formation of 14-hydroxycodeinone—the actual ABUK impurity one is trying to eliminate—during the formation and in the presence of oxycodone, and in some cases, oxycodone hydrochloride. Accordingly, new methods of producing oxycodone and its salts with low levels of impurities, including ABUK, would be beneficial.

A novel process is now disclosed for producing oxycodone and its salts, especially, oxycodone hydrochloride, with low levels of impurities, including ABUK, that diverges from the approaches described above. All of the patents, published patent applications, journal articles, and other references cited in the present disclosure are incorporated by reference herein in their entireties for all useful purposes.

In brief, the inventors have found, among other things, that reduction of the ketone group of 14-hydroxycodeinone to afford 14-hydroxycodeine also reduces the ketone groups of 8,14-dihydroxy-7,8-dihydrocodeinone, thereby converting the diols to 8,14-dihydroxy-7,8-dihydrocodein-6-ol. An exemplary sequence of steps according to preferred embodiments of the invention is shown in Schemes 1 and 2. As shown, after oxidation and reduction steps, a rearrangement step for producing oxycodone free base is used to significantly reduce or eliminate impurities, including especially ABUK, prior to converting the oxycodone free base to its salt. Also described are several optional purification steps, and a salt formation step.

DETAILED DESCRIPTION OF THE INVENTION

It is known that oxidation reactions of commercially available varieties of thebaine will produce 14-hydroxycodeinone. This is described, for example, by Chapman and Cox as well as in U.S. Pat. No. 7,153,966 of Casner. During oxidation, especially under aqueous acidic conditions, the two isomers of 8,14-dihydroxy-7,8-dihydrocodeinone are also formed as impurities. See, e.g., Proska, Arch. Pharm. Pharm. Med. Chem., 332, 369-70 (1999). Next, the ketone of 14-hydroxycodeinone is reduced to form 14-hydroxycodeine and, as a consequence of the reduction, the ketones of the two isomers of 8,14-dihydroxy-7,8-dihydrocodeinone are also reduced, creating related 8,14-dihydroxy-7,8-dihydrocodein-6-ol isomers, or triols. Only traces of the two isomers of the diols remain and these are purged when the oxycodone base is purified prior to salt formation.

In a novel metal-catalyzed process, 14-hydroxycodeine is rearranged to oxycodone in a reaction whereby the 6-hydroxyl group is oxidized and the 7,8 double bond is reduced. Because the two isomers of 8,14-dihydroxy-7,8-dihydrocodein-6-ol do not have the allylic C6, C7, C8 topography contained within 14-hydroxycodeine, they do not participate in the rearrangement. The triols are observed in the resulting oxycodone. The triols also do not appear to interfere and therefore cannot convert to 14-hydroxycodeinone. In this sense, they are inert with regard to conversion to either 14-hydroxycodeinone or oxycodone. Moreover, the triols are far more polar than oxycodone and can potentially be separated from oxycodone by precipitating the oxycodone from a polar solvent or solvent mixture, or by extracting oxycodone into a suitable organic solvent. Notwithstanding, even if some of the triols were to remain with oxycodone, these species lack the purportedly genotoxic alpha, beta unsaturated ketone, cannot generate it, and do not fall under FDA alert compound status. When the resulting oxycodone base is converted to the hydrochloride salt, the active, alpha diol is not present and any traces of the triols are incapable of generating 14-hydroxycodeinone, so the salt can be produced without risk of regenerating that impurity.

Scheme 1. Synthetic Route To Oxycodone Base and Oxycodone Hydrochloride

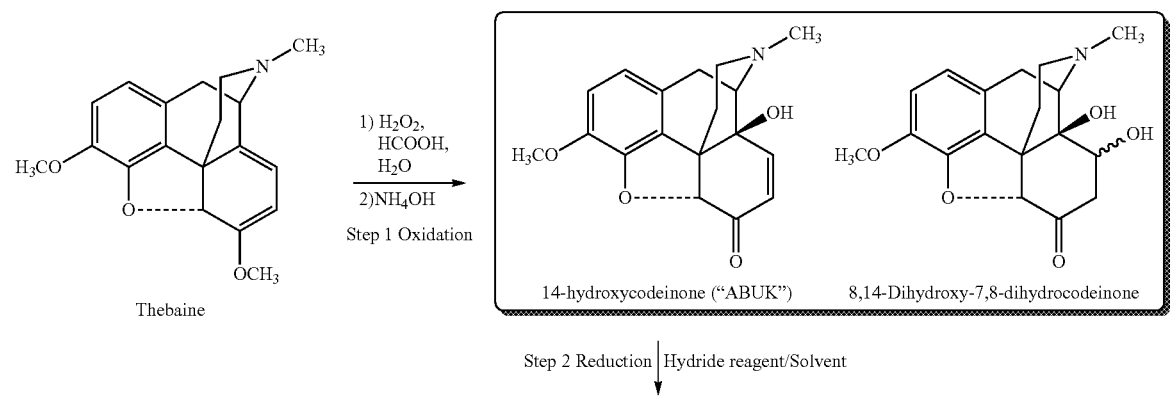

-continued

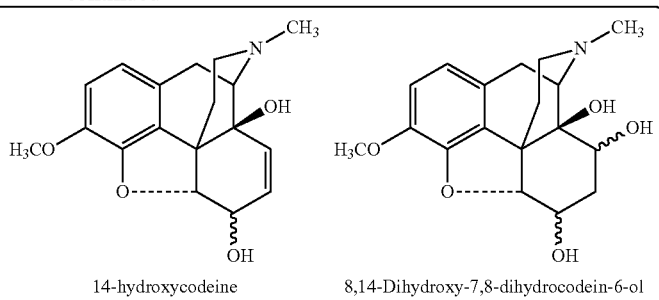

14-hydroxycodeine     8,14-Dihydroxy-7,8-dihydrocodein-6-ol

Step 3 Rearrangement | Metal catalyst/Solvent

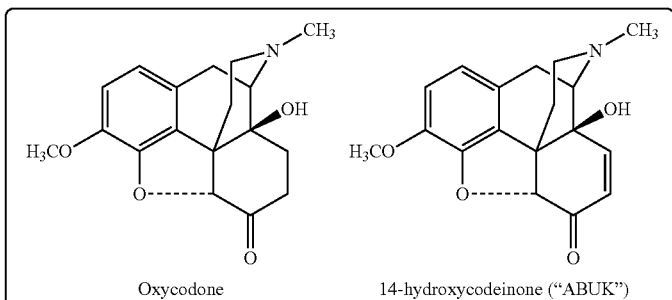

Oxycodone     14-hydroxycodeinone ("ABUK")

Step 4 Purification | 1. $Na_2S_2O_5$, pH 7, r.t.
2. $NH_4OH$ to pH 9

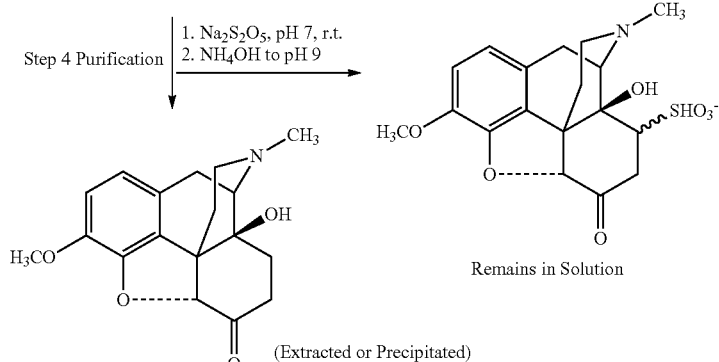

(Extracted or Precipitated)

Low ABUK Base
Undected (<2 ppm) a-diol
<5 ppm 14-hydroxycodeinone

Remains in Solution

Step 5 Salt Formation | Alcohol, aq. HCl

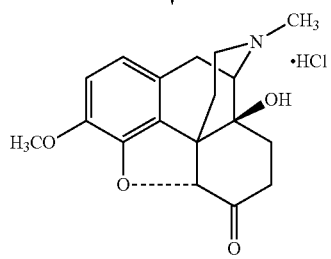

Low ABUK Oxycodone HCl
<5 ppm 14-hydroxycodeinone

Scheme 2: Alternative Routes from Crude Oxycodone Base to Low ABUK Oxycodone HCl

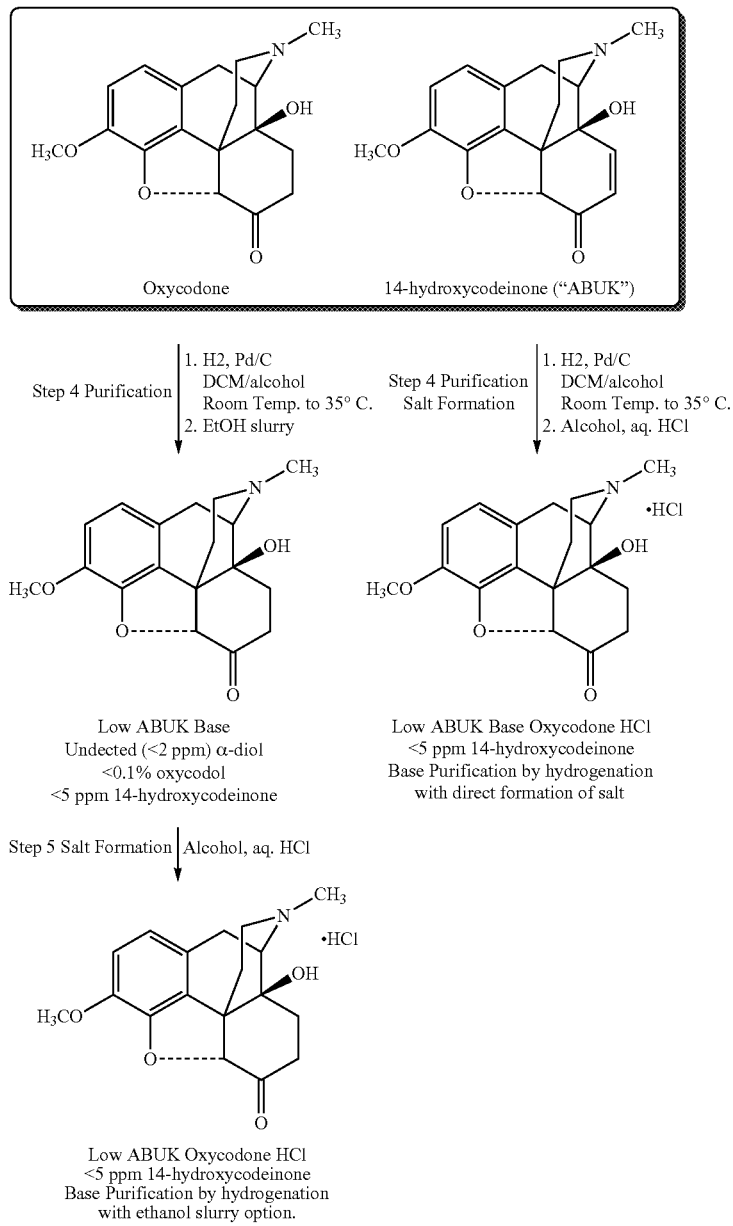

Oxidation of thebaine to 14-hydroxycodeinone may be performed by any means known in the art, for example as described in U.S. Patent Application Publication No. 2006/0111383 to Casner et al. Reduction of 14-hydroxycodeinone to 14-hydroxycodeine may involve any method known in the art for reducing ketone groups of alpha, beta unsaturated ketones, with sodium borohydride being one example as described below.

Suitable catalysts for Step 3 of Scheme 1 include any of a variety of ligand-complexed metal catalyst, including such catalysts wherein the ligand is a phosphine and the metal is rhodium or ruthenium. Wilkinson's catalyst and analogs thereof are generally suitable. Specific examples of suitable catalysts are disclosed in U.S. Pat. No. 7,323,565 and U.S. Pat. No. 7,321,038 to Wang et al. One suitable catalyst is shown below, the preparation and use of which is detailed in the Examples herein.

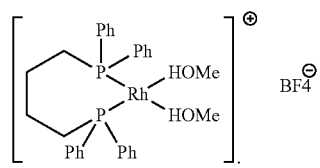

The new route to oxycodone enjoys several advantages over the aforementioned routes as per Chapman, Shafer, Buehler, and Cox. The process converts known precursors of the purportedly genotoxic 14-hydroxycodeinone to triol species that are incapable of giving rise to this impurity. This conversion may be performed concurrently with the conversion of 14-hydroxycodeinone to 14-hydroxycodeine (i.e., before converting the 14-hydroxycodeine to oxycodone). The 14-hydroxycodeine may be isolated as a solid or extracted into a suitable organic solvent, either approach allowing the opportunity to purge these triols a full chemical stage before oxycodone is formed. In some examples trace levels of 8β,14-dihydroxy-7,8-dihydrocodeinone are observed by LC/MS in the isolated 14-hydroxycodeine; however, 8α,14-dihydroxy-7,8-dihydrocodeinone is not detectable at this stage of the process. In a further embodiment of the invention, the 14-hydroxycodeine may be treated with sodium meta-bisulfate as per Rappoport et al., J. Amer. Chem. Soc. 89:8, 1967, 1942-1947, 1 or similar species as a means to remove any remaining traces of 14-hydroxycodeinone or of the ketone-containing diols. In still a further embodiment, the 14-hydroxycodeine may be treated with resin-supported borohydride to remove any trace amounts of 14-hydroxycodeinone. In yet another embodiment of the invention, residual 14-hydroxycodeine may be treated with organic thiol species to selectively form water-soluble or resin bound derivatives of any remains 14-hydroxycodeinone such that 14-hydroxycodeine may be produced free of 14-hydroxycodeinone. By means of the reducing step and, optionally, the incorporation of treatments using meta-bisulfite-related or thiol-type species, 14-hydroxycodeine substantially free of residual 14-hydroxycodeinone and of the two diols can be produced. In another embodiment, any trace amounts of 14-hydroxycodeinone in 14-hydroxycodeine are carried through the rearrangement step and removed from the oxycodone base by catalytic hydrogenation in an organic solvent.

As will be understood from the above explanation, diols that are potential precursors to 14-hydroxycodeinone are not converted to that compound, but instead are converted to species that are incapable of giving rise to 14-hydroxycodeinone. In this fashion, the drug entity is not actively contaminated with the purportedly genotoxic impurity one is also trying to remove.

It is noteworthy that 14-hydroxycodeinone is both the undesired, purportedly genotoxic species and the penultimate intermediate common to most traditional syntheses of oxycodone. Conventional synthesis routes rely upon hydrogenation of 14-hydroxycodeinone to form oxycodone, and the hydrogenation may often be left incomplete such that large amounts of 14-hydroxycodeinone—1,000-5,000 ppm—are carried forward directly into the isolated oxycodone. See, e.g. U.S. Pat. No. 7,674,800, Examples 2 and 3). The aforementioned approaches may thus be burdened by the need to overcome this reservoir of 14-hydroxycodeinone carried forward along with that formed by forced dehydration of the diols. In contrast, the new process converts 14-hydroxycodeinone to a new, non-ketone intermediate (i.e., 14-hydroxycodeine) with zero or low single digit ppm levels of remaining 14-hydroxycodeinone. Should non-zero levels of 14-hydroxycodeinone remain, these can be removed as described above using meta-bisulfite or organic thiol agents. Alternatively, 14-hydroxycodeinone can be removed from oxycodone base by catalytic hydrogenation in an organic solvent or a mixture of solvents.

The new route employs what is believed to be a novel rearrangement of a C-14 oxidized codeine-like entity to oxycodone. There are many published reports for the rearrangements of 6-hydroxy 7,8 double bond allylic systems such as found in codeine to form, for example, hydrocodone. However, the inventors are not aware of any reports of a similar rearrangement of related species bearing the 14-hydroxy group. Indeed, 14-hydroxycodeine, the intermediate in the new process disclosed here, is a "bisallylic" entity to the extent that the 7,8 double bond and 14-hydroxylic moiety constitute a second allylic function. The lack of reports of metal-catalyzed rearrangements of C-14 hydroxyl analogues of codeine to form the 6-ketone function suggests that those skilled in the art would not expect this to be a particularly productive, or even probable, reaction.

The reduction of 14-hydroxycodeinone to 14-hydroxycodeine is expected to entirely convert the diols to the triols. 14-hydroxycodeine containing ca. 0-50 ppm of 14-hydroxycodeinone will undergo a metal catalyzed rearrangement to form oxycodone base with about 45-350 ppm of 14-hydroxycodeinone. LC/MS analysis indicates that the presumed active diol, 8α,14-dihydroxy-7,8-dihydrocodeinone, may be present at up to 16 ppm while 8β,14-dihydroxy-7,8-dihydrocodeinone may be present, with two other species having molecular weights matching the triols, at up to about 110 ppm. The minor increase in 14-hydroxycodeinone is thought to result from very slow oxidation of oxycodone by the metal rearrangement catalyst. This is supported by the fact that the inventors have demonstrated that oxycodone with undetectable (or, at most, single digit ppm) levels of either isomer of 8α,14-dihydroxy-7,8-dihydrocodeinone will slowly give rise to 14-hydroxycodeinone upon exposure to the metal rearrangement catalyst under conditions of the rearrangement to levels of over 60 ppm, far higher than levels obtainable from the quantity of diols present. The very low levels of 14-hydroxycodeinone observed in oxycodone formed by the current invention are, however, in sharp contrast to the high levels found in oxycodone produced by the aforementioned processes, as noted above, which may contain 1,000-5,000 ppm of 14-hydroxycodeinone, and the potential for more due to the 1000 ppm or more of each of the diol precursors to 14-hydroxycodeinone, i.e., 8α,14-dihydroxy-7,8-dihydrocodeinone and 8β,14-dihydroxy-7,8-dihydrocodeinone. The traces of the 8α,14-dihydroxy-7,8-dihydrocodeinone and 8β,14-dihydroxy-7,8-dihydrocodeinone observed after the rhodium catalyzed rearrangement are purged in the next stage of the process while purifying the oxycodone base.

Oxycodone base prepared by the new process, containing ca. 0-350 ppm of 14-hydroxycodeinone, can be rendered virtually free of this impurity by following a purification process such as the sodium meta-bisulfite procedure described by Rappoport et al., J. Amer. Chem. Soc. 89:8, 1967, 1942-1947. This affords an oxycodone free base having undetectable (or, at most, very low) levels of 14-hydroxycodeinone. Alternatively, one may reduce the residual 14-hydroxycodeinone to levels under 5 ppm by catalytic hydrogenation using a palladium on carbon catalyst in an organic solvent or solvent mixture. The hydrogenation may be run at about 13-50 psi and at temperatures from about room temperature (e.g., 18° C.) to about 40° C. Suitable catalysts include, but are not limited to, 5% and 10% palladium on carbon. Suitable solvents include alcohols, chlorinated solvents, or mixtures thereof. The isolation of the hydrogenated oxycodone as a solid purges most of any residual trace amounts of 8α,14-dihydroxy-7,8-dihydrocodeinone and 8β,14-dihydroxy-7,8-dihydrocodeinone.

The exposure of oxycodone to hydrogenation conditions has been found to produce low levels of 6-hydroxy oxycodol. This is removed using an ethanol slurry, preferably at an elevated temperature, with the added benefit of also removing any further trace amounts of 14-hydroxycodeinone, 8α,14-dihydroxy-7,8-dihydrocodeinone, and 8β,14-dihydroxy-7,8-dihydrocodeinone in the unslurried oxycodone base. Purified oxycodone base produced via a rhodium-catalyzed rearrangement reaction of 14-hydroxycodeine, subsequent hydrogenation and an ethanol slurry contains no detectable amounts of 8α,14-dihydroxy-7,8-dihydrocodeinone, ca. 10 ppm of 8β,14-dihydroxy-7,8-dihydrocodeinone, and 1-5 ppm of 14-hydroxycodeinone.

In a further embodiment, crude oxycodone base containing traces of 14-hydroxycodeine may be purified by hydrogenation as described above, and used as a solution after catalyst filtration to form and isolate oxycodone HCl salt having less than 5 ppm of residual 14-hydroxycodeinone.

Importantly, unlike the Buehler, Cox, Chapman, or Shafer processes, the new process does not require breaking down the diol precursors to form 14-hydroxycodeinone in the presence of oxycodone. There is also no threat that unconverted 8α,14-dihydroxy-7,8-dihydrocodeinone will be carried into the oxycodone product and pose a risk of regenerating 14-hydroxycodeinone during salt formation, stability testing or upon storage. Again, this is in contrast to aforementioned processes. For example, as noted by Chapman in Example 3, care is required when handling the HCl salt from the base in the route described there due to the possible presence of unconverted diol precursors. These precursors can convert to 14-hydroxycodeinone during salt formation or on storage or stability testing. Because 8α,14-dihydroxy-7,8-dihydrocodeinone is undetected in oxycodone base prepared by the new process, no possibility exists to regenerate 14-hydroxycodeinone from it while making the HCl salt. The conversion of oxycodone base produced by the process above, and containing less than 5 ppm 14-hydroxycodeinone and no detectable 8α,14-dihydroxy-7,8-dihydrocodeinone, showed no change in the level of 14-hydroxycodeinone level in the isolated oxycodone HCl salt. Furthermore, treatment of the oxycodone base or oxycodone HCl salt made by the above process in 65° C. aq. hydrochloride acid at pH<1 resulted in no or minimal growth in 14-hydroxycodeinone after 24 hours. Exposure of oxycodone base and oxycodone HCl salt made by the above process to conditions of dry heat (greater than 60° C.) resulted in no growth of 14-hydroxycodeinone after 14 days. In view of assertions noted above by Baldwin regarding the ease of dehydration of 8α,14-dihydroxy-7,8-dihydrocodeinone in weak acid (i.e., 0.2N; U.S. Pat. No. 7,674,800, Example 3), the slow, trace growth observed in hot acid is attributable to trace levels of residual 8β,14-dihydroxy-7,8-dihydrocodeinone as per Weiss, or to other unknown precursors to 14-hydroxycodeinone. This stability provides wider process latitude during oxycodone salt formation on an industrial scale and suggests a highly stable solid product with regard to growth of 14-hydroxycodeinone.

EXAMPLES

Example 1

Reduction of 14-hydroxycodeinone to 14-hydroxycodeine

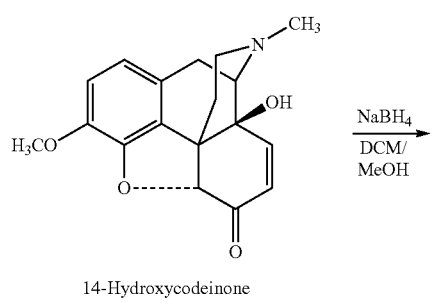

14-Hydroxycodeinone

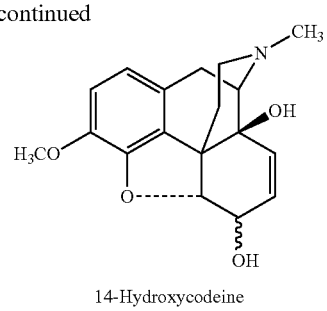

14-Hydroxycodeine

A portion of 14-hydroxycodeinone (26.0 g wet, 16.9 g dry weight, 54.0 mmol) was combined with 135 ml methylene chloride and 15 ml methanol under nitrogen in a round bottomed flask equipped with a thermometer. The slurry was cooled to 0-5° C. in an ice bath. Sodium borohydride (2.54 g, 66.8 mmol) was added to the slurry in one portion. Excess hydrogen was released through a bubbler, and the reaction mixture was allowed to warm up to ambient temperature and was stirred for 48 hours.

After the starting material was consumed, the excess sodium borohydride was quenched with 70 ml 10 wt % hydrochloric acid. The aqueous layer was at pH=1. The two phase mixture was stirred for one hour. The layers were separated and the upper aqueous layer was separated from the lower organic layer. The organic layer was washed with distilled water (2×20 ml). The aqueous layers were combined and the pH was adjusted to 9 with the addition of 45 ml of 5 M sodium hydroxide solution. An oily precipitate formed and the aqueous slurry was extracted with dichloromethane (3×50 ml). The combined dichloromethane phase was washed with 20% sodium chloride solution, dried over sodium sulfate, filtered and evaporated yielding 15.1 g (89%) brown oil which solidified upon standing. Trituration of the solidified oil with cold 2-propanol afforded 12.5 g (74%) white crystalline 14-hydroxycodeine.

Example 2

Rearrangement of 14-hydroxycodeine to Oxycodone

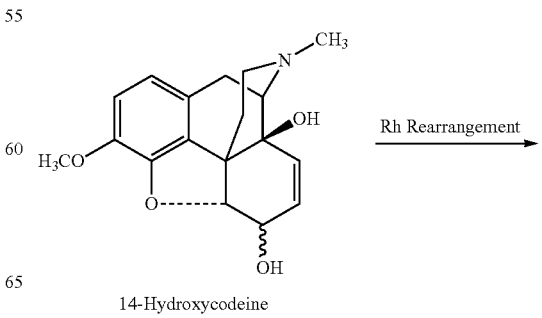

14-Hydroxycodeine

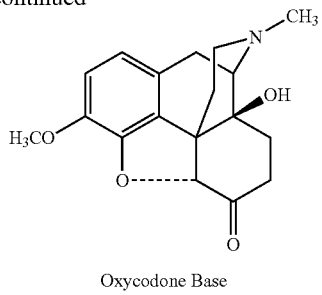

Oxycodone Base

A 100 ml 4 necked round bottom flask, equipped with condenser and a gas sparging tube, gas outlet and a thermometer, was flushed with nitrogen and charged with methanol (40 ml). A portion of 14-Hydroxycodeine (5.0 g, 15.9 mmol) was added at room temperature and the mixture was stirred until a homogenous solution formed. The solution was deoxygenated by sparging with nitrogen gas while stirring.

A 20 ml Schlenk flask, equipped with a gas sparging tube and gas outlet, was flushed with nitrogen and charged with methanol (10 ml). The solvent was deoxygenated by sparging nitrogen gas through it while stirring. Bis(norbornadiene) rhodium (I) tetrafluoroborate (70 mg, 0.19 mmol) and 1,4-bis (diphenylphosphino)butane (80 mg, 0.19 mmol) were added under nitrogen and the orange solution was stirred at room temperature for 30 minutes. The solution was then sparged with hydrogen gas for 30 minutes. The color of the solution changed from orange to dark reddish orange. Excess hydrogen was removed by sparging the solution with nitrogen for 10 minutes. The solution of the catalyst was transferred to the solution of 14-hydroxycodeine via cannula. The combined solution was heated at 50° C. for 90 minutes. The product, oxycodone free base, precipitated from the reaction mixture and a thick slurry formed. A small sample was taken for an in-process test to confirm the reaction completion. The reaction mixture was cooled to 0-5° C. for 2 hours, and the product was filtered off and washed with 10 ml cold 2-propanol.

The product, oxycodone free base, was dried in a vacuum oven at 50° C. Yield: 4.1 g, 71.9%.

Example 3

Removal of 14-hydroxycodeinone from 14-hydroxycodeine

A 100 ml round bottom flask, equipped with gas outlet and a thermometer, was flushed with nitrogen and charged with methanol (40 ml). 14-Hydroxycodeine (5.0 g, 15.9 mmol) containing a small amount of 14-hydroxycodeinone as an impurity was added at room temperature and the mixture was stirred until a homogenous solution formed.

Resin supported borohydride (0.15 g) was added to the solution and it was stirred for 24 h at 55° C. A small sample was taken for the in process test to confirm the removal of 14-hydroxycodeinone. The mixture was then filtered through 45 μm filter under nitrogen blanket into a 100 ml 4 necked round bottom flask, equipped with condenser and a gas sparging tube, gas outlet, and a thermometer. The solution was deoxygenated by sparging nitrogen gas through it while stirring, for use in Example 4.

Example 4

Rearrangement of 14-hydroxycodeine to Oxycodone

A 20 ml Schlenk flask, equipped with a gas sparging tube and gas outlet, was flushed with nitrogen and charged with methanol (10 ml). The solvent was deoxygenated by sparging nitrogen gas through it while stirring. Bis(norbornadiene) rhodium (I) tetrafluoroborate (70 mg, 0.19 mmol) and 1,4-bis (diphenylphosphino)butane (80 mg, 0.19 mmol) were added under nitrogen and the orange solution was stirred at room temperature for 30 minutes. The solution was then sparged with hydrogen gas for 30 minutes. The color of the solution changed from orange to dark reddish orange. Excess hydrogen was removed by sparging the solution with nitrogen for 10 minutes. The solution of the catalyst was transferred to the solution of 14-hydroxycodeine from Example 3 via cannula. The combined solution was heated at 50° C. for 90 minutes. Oxycodone free base precipitated from the reaction mixture and a thick slurry formed. A small sample was taken for an in-process test to confirm the reaction completion. The reaction mixture was cooled to 0-5° C. for 2 hours and the product was filtered off, washed with 10 ml cold 2-propanol.

The product, oxycodone free base, was dried in a vacuum oven at 50° C. Yield: 3.43 g, 68.6%.

Example 5

Reduction of 14-Hydroxycodeinone to 14-Hydroxycodeine

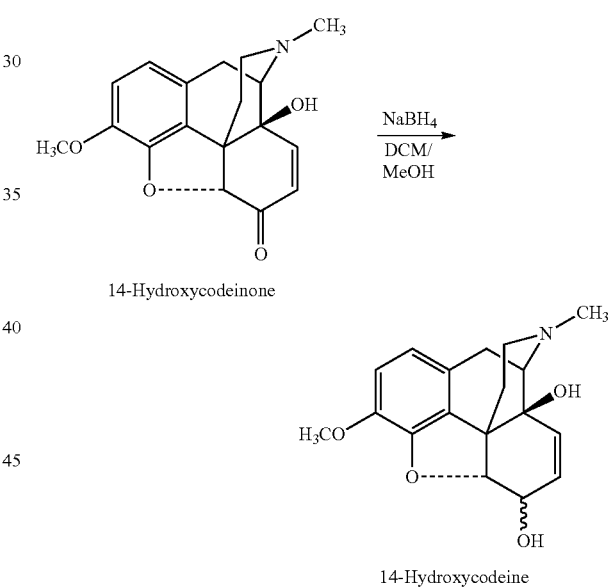

14-Hydroxycodeinone (25.0 g wet, 22.225 g dry weight, 70.93 mmol) was combined with 178 mL methylene chloride and 13 mL methanol under nitrogen in a round bottomed flask equipped with a thermometer and a solution resulted. The batch was cooled to 0-5° C. in an ice bath. Sodium borohydride (3.44 g, 90.93 mmol) was added in one portion. The mixture was stirred at 0-5° C. for 7 hours and then allowed to warm up to ambient temperature and stirred for 17 hours. After the starting material was consumed, the excess sodium borohydride was quenched with 110 mL of 2.4N hydrochloric acid at 0-5° C. The aqueous layer was at pH=1. The two phase mixture was stirred at 0-5° C. for 30 min. The layers were settled and separated. The upper aqueous layer was separated from the lower organic layer. The organic layer was washed with 15 mL of 2.4N hydrochloric acid. The aqueous layers were combined and the pH was adjusted to 9.5 with the addition of 30 mL of 25% sodium hydroxide solution at <10° C. There was no precipitate formed in the beginning at 10° C. The ice/water bath was then removed and the batch was stirred at ambient temperature. Solids precipitated at the overnight agitation. The batch was cooled to 0-5° C. and stirred for 1.5 h. Product was filtered, rinsed with cold water (25 mL×2), and dried. 8.99 g (40.2%) of off-white solid was obtained as Lot 2377-085 (4 ppm 14-hydroxycodeinone).

Example 6

Rearrangement of 14-Hydroxycodeine to Oxycodone Base

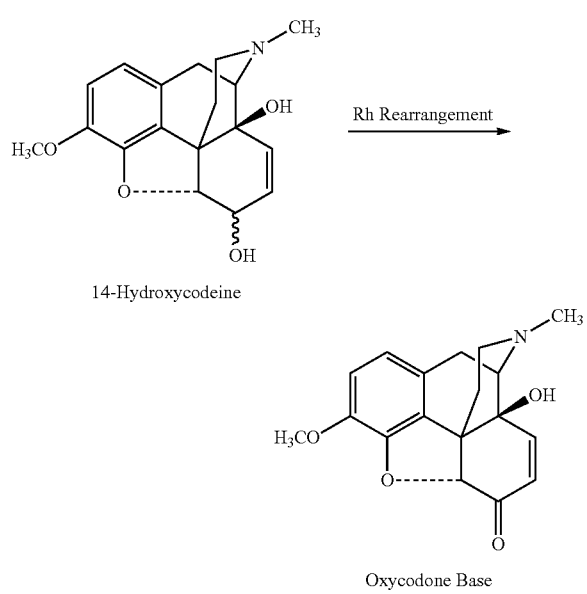

An oven-dried 100 mL round bottom flask was charged with 5 g 14-hydroxycodeine (15.9 mmol, Lot 2377-085) and 40 mL of deoxygenated methanol. The mixture was stirred under nitrogen until homogenous solution formed.

An oven-dried 25 mL round bottom flask was charged with 10 mL of deoxygenated methanol and placed under nitrogen. 75 mg of bis(norbornadiene)rhodium (I) tetrafluoroborate (0.2 mmol) and 86 mg of 1,4-bis(diphenylphosphino)butane (0.2 mmol) were added under nitrogen and the orange solution was stirred at RT for 10 minutes. The solution was then sparged with hydrogen gas for 45 minutes. The color of the solution changed from orange to reddish orange. Excess hydrogen was removed by sparging the solution with nitrogen for 10 minutes. The solution of the catalyst was transferred to the solution of 14-hydroxycodeine via cannula. The combined solution was heated at 50° C. for 9 hours. The product, Oxycodone free base, precipitated from the reaction mixture and a thick slurry formed. A small sample of the supernatant was taken for the in process test to confirm the reaction completion.

The reaction mixture was cooled to 0-5° C. for 2 hours and the product was filtered off, and the filter cake washed with cold ethanol (10 mL×2).

The product was dried in a vacuum oven at 55° C. 1.71 g (34.2% yield, as Lot 2377-095) of oxycodone base was obtained. (45 ppm 14-hydroxycodeinone, undetected 8α,14-dihydroxy-7,8-dihydrocodeinone by LC/MS and 5 ppm 8β,14-dihydroxy-7,8-dihydrocodeinone by LC/MS; 99.41A % pure by HPLC).

Example 7

Purification of Oxycodone Base by Sodium Metabisulfite

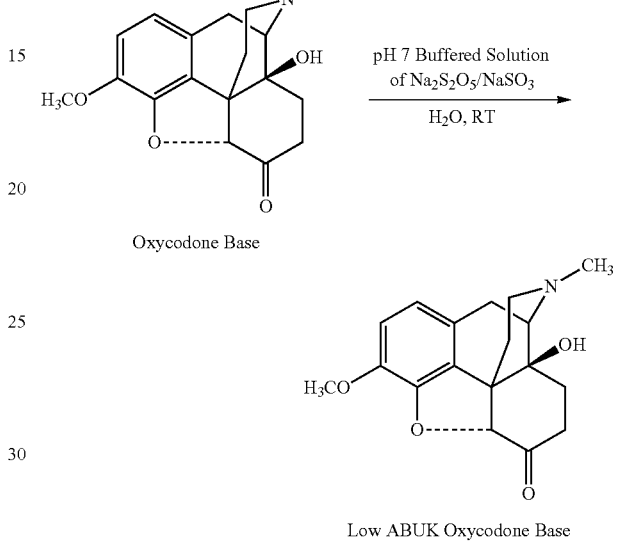

To a 25 mL flask is charged 1.5 g (4.756 mmol, Lot 2377-095, prepared via Rh catalyst rearrangement) of oxycodone base and 7.5 mL of water. The mixture is stirred at room temperature (RT, 20±5° C.). pH is 8.45, which is then adjusted to 7.02 at RT by adding 0.056 g of conc. HCl.

Preparation of pH 7 $Na_2S_2O_5/Na_2SO_3$ buffered solution: To a small flask is charged 0.362 g of sodium meta-bisulfite (1.904 mmol, 0.4 eq) and 1 mL of water. Stirred at RT and a clear solution resulted within 4 min (pH-4-5). To another small flask, 1.43 g (11.35 mmol) of sodium sulfite and 6 mL water are charged. The mixture is stirred at RT and a clear solution resulted within 4 min (pH~9-10). The sodium meta-bisulfite solution is transferred to sodium sulfite solution at RT and stirred. The pH is 6.90, which is then adjusted to 6.97 at RT by adding 1.43 g of saturated sodium sulfite solution.

The pH 7 buffered solution of sodium meta-bisulfite/sodium sulfite prepared above is transferred to the batch at RT. The pH went up to 7.98, which is then adjusted to 7.01 at RT by adding 0.777 g of conc. HCl. A solution results. The mixture is stirred at RT for 3-24 h, or until the reaction is complete. (In-process test for reaction completion by LC/MS: ≤1 ppm 14-hydroxycodeinone.) pH is adjusted to 9.18 by adding 0.95 g (1.1 mL) of conc. ammonium hydroxide. The mixture (a white slurry) is stirred at RT for 2 h, filtered, washed with water (6 mL×2) and dried until transferable.

The wet cake is transferred to a 25 mL flask, slurried in 12 mL water for 2 h, filtered, washed with water (6 mL×2), and dried until weight is constant. 1.34 g (89.3% yield) of low ABUK oxycodone base is obtained, as Lot 2377-103 (~1 ppm 14-hydroxycodeinone by LC/MS, undetected 8α,14-dihydroxy-7,8-dihydrocodeinone by LC/MS and 4 ppm 8β,14-dihydroxy-7,8-dihydrocodeinone by LC/MS; 99.48A % pure by HPLC).

Example 8A

Purification of Oxycodone Base by Hydrogenation

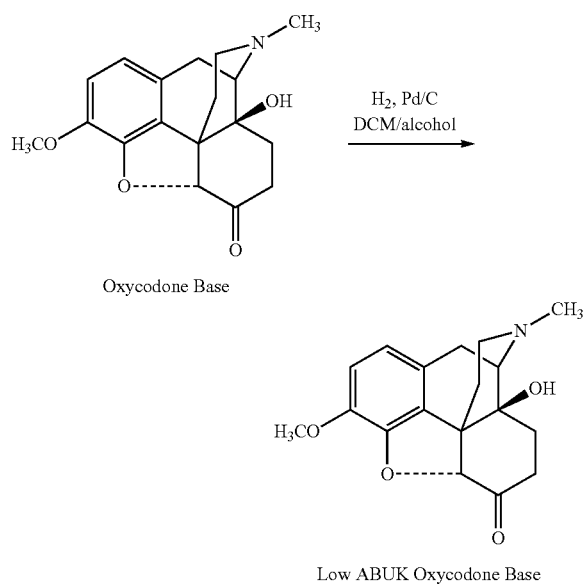

Oxycodone Base

Low ABUK Oxycodone Base

To a 250 mL hydrogenation bottle was charged 4.05 g (12.84 mmol, prepared via the Rh-catalyzed rearrangement, 267 ppm 14-hydroxycodeinone; 16 ppm 8α,14-dihydroxy-7,8-dihydrocodeinone, 111 ppm of 8β,14-dihydroxy-7,8-dihydrocodeinone) of oxycodone base, 36 mL of dichloromethane (DCM) and 4 mL of methanol. The mixture was agitate until a clear solution was formed, and 0.4 g of 5% Pd/C was added. The mixture was hydrogenated with agitation at 21-22° C. (room temperature), 13-17 psi $H_2$ and was processed in portions to isolated oxycodone base after one and two days of hydrogenation.

After one day under hydrogenation conditions, about 16 mL of the mixture was removed from hydrogenation bottle, catalyst was filtered was removed by filtration, and the filtered solution was concentrated by distilling off DCM/methanol. After most of the DCM/methanol had been removed, isopropanol (IPA) was added and the mixture was distilled at 65-70° C. for 10 min. The mixture was cooled to room temperature and then to 0-5° C. The product was isolated by filtration, rinsed and dried. 1.359 g of low ABUK oxycodone base was obtained. (2.4 ppm 14-hydroxycodeinone by LC/MS; undetected 8α,14-dihydroxy-7,8-dihydrocodeinone by LC/MS, 28 ppm 8β,14-dihydroxy-7,8-dihydrocodeinone by LC/MS; 97.61A % pure by HPLC).

After the second day under hydrogenation conditions, the rest of the mixture was filtered to remove catalyst was and the DCM/methanol was removed by distillation. After most DCM/methanol had been removed, IPA and continued the mixture was distilled at 75-76° C. for 10 min. The mixture was cooled to room temperature and then to 0-5° C. The product was isolated by filtration, rinsed and dried. 2.442 g of low ABUK oxycodone base was obtained (2.7 ppm 14-hydroxycodeinone by LC/MS, 3 ppm 8α,14-dihydroxy-7,8-di-hydrocodeinone by LC/MS, 41 ppm 8β,14-dihydroxy-7,8-dihydrocodeinone by LC/MS; 97.67A % pure by HPLC).

Example 8B

Purification of Crude Oxycodone Base by Hydrogenation at 35° C.

To a 250 mL hydrogenation bottle was charged 5.0 g (15.85 mmol, prepared via the Rh-catalyzed rearrangement, 267 ppm 14-hydroxycodeinone; 16 ppm 8 alph, 11 ppm of 8 beta) of oxycodone base, 30 mL of dichloromethane (DCM) and 10 mL of isopropanol (IPA). The mixture was agitated until a clear solution was formed, and 0.5 g of 5% Pd/C was added. The mixture was hydrogenated with agitation at 35° C., ca. 25 psi $H_2$ for one day. The catalyst was removed by filtration, and the filtered solution was concentrated by distilling off DCM/IPA. After most of the DCM/IPA had been removed, 3 mL of isopropanol (IPA) was added and the mixture was distilled at 65-70° C. for 5 min. The mixture was cooled to room temperature and then to 0-5° C. The product was isolated by filtration, rinsed with cold IPA, and dried. The low ABUK oxycodone base obtained showed 1.5 ppm 14-hydroxycodeinone by LC/MS; undetected 8α,14-dihydroxy-7,8-dihydrocodeinone by LC/MS, 27 ppm 8β,14-dihydroxy-7,8-dihydrocodeinone by LC/MS; 0.86 HPLC A % 6-oxycodol 98.87A % pure by HPLC.

Example 9

Purification of Low ABUK Oxycodone Base by Ethanol Slurry

To a 50 mL flask was charged 3.986 g (12.64 mmoles) of low ABUK oxycodone base prepared by combining the sample from Examples 8 and 8A (purified via hydrogenation) (composite: 2 ppm 8α,14-dihydroxy-7,8-dihydrocodeinone, 35 ppm 8α,14-dihydroxy-7,8-dihydrocodeinone, 1.06A % 6-oxycodol, 98.42A % pure by HPLC) and 24 mL of denatured ethanol (SDA3A). The mixture (slurry) was heated to reflux for 1.5 h, cooled to RT, and then 0-5° C. Solid was isolated by filtration, rinsed and dried. 3.307 g of purified low ABUK oxycodone base was obtained (2.7 ppm 14-hydroxycodeinone, undetected 8α,14-dihydroxy-7,8-dihydrocodeinone by LC/MS, 11 ppm 8β,14-dihydroxy-7,8-dihydrocodeinone by LC/MS, 0.21 HPLC A % 6-oxycodol; 99.71A % pure by HPLC).

Example 10

Conversion of Purified Low ABUK Oxycodone Base to Oxycodone Hydrochloride Salt

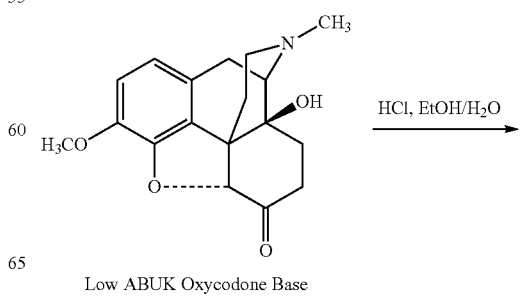

Low ABUK Oxycodone Base

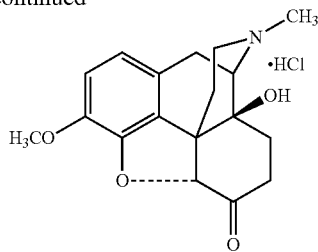

Low ABUK Oxycodone HCl

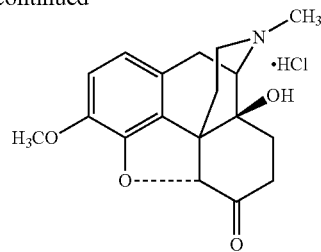

Low ABUK Oxycodone HCl

To a 10 mL flask is charged 1.0 g (3.17 mmol, Lot 2377-103) of oxycodone base (from Example 7) 3.2 mL ethanol and 0.63 mL of water. The mixture is stirred at room temperature (RT, 20±5° C.). A slurry is resulted. The batch is heated to 45° C., added 0.326 g (3.31 mmol, 1.044 molar equivalents) of 37% hydrochloric acid, and a solution is then resulted. The mixture is heated to 55° C. and stirred at 55° C. for 10 hours. Cooled to RT and then to 0-5° C. The mixture is stirred at 0-5° C. for 1.5 hours, filtered, rinsed with cold ethanol (2 mL×2) and dried. 1.021 g of oxycodone HCl (91.4% yield, as Lot 2377-107) is obtained. (3 ppm 14-hydroxycodeinone, undetected 8α,14-dihydroxy-7,8-dihydrocodeinone by LC/MS, and 8β,14-dihydroxy-7,8-dihydrocodeinone by LC/MS; 99.84A % pure by HPLC).

Example 11

Conversion of Purified, Low ABUK Oxycodone Base to Oxycodone Hydrochloride Salt

To a 25 mL flask was charged 2.0 g (6.34 mmol, from Example 9) of low ABUK oxycodone base, 6.4 mL of ethanol and 1.3 mL of water. The mixture was stirred at RT. The batch was heated to 41-46° C., added 0.643 g (6.527 mmol, 1.03 molar equivalents) of 37% hydrochloric acid, and a solution was then resulted. The mixture was heated to 55° C. and stirred at 55° C. for 10 hours to simulate the production salt formation timeframe. The mixture was cooled to room temperature and then to 0-5° C. The mixture was stirred at 0-5° C. for 1.5 hours, filtered, and the product on the filter was rinsed with cold ethanol (2.5 mL×2) and dried. 1.899 g of oxycodone HCl (85.12% yield, as Lot 2418-123) was obtained (2.5 ppm 14-hydroxycodeinone by LC/MS, undetected 8α,14-dihydroxy-7,8-dihydrocodeinone by LC/MS and 8β,14-dihydroxy-7,8-dihydrocodeinone by LC/MS; 0.01 HPLC A % 6-oxycodol; 99.93 HPLC A % oxycodone HCl).

Example 12

Telescoped Conversion of Crude Oxycodone Base to Low ABUK Oxycodone HCl Salt

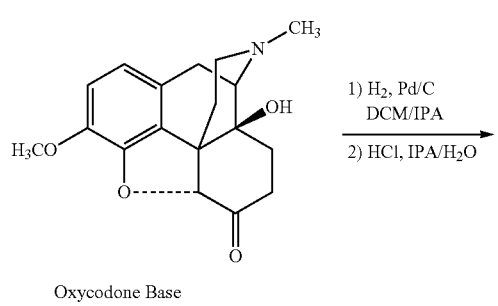

Oxycodone Base

1) $H_2$, Pd/C
DCM/IPA
2) HCl, IPA/$H_2O$

To a 250 mL hydrogenation bottle was charged 1.5 g (4.75 mmol, prepared via Rh catalyst rearrangement, 424 ppm 14-hydroxycodeinone) of oxycodone base, 6 mL of dichloromethane (DCM) and 2 mL of isopropanol (IPA). The mixture was agitated until a solution was obtained, then 0.15 g of 10% Pd/C was added. The mixture was hydrogenated with agitation at 35° C., 25 psi $H_2$ and processed to isolated oxycodone HCl in portions after one and two days of hydrogenation.

After one day of hydrogenation, about 1.5 mL of the mixture was removed from hydrogenation bottle and filtered to remove catalyst. The filtered mixture was distilled to minimize the solvents (DCM/IPA). The batch was diluted with 1.2 mL of IPA, 0.4 mL of water and 0.105 g of 37% hydrochloric acid (1.066 mmol), and stirred at ambient temperature. The mixture was then heated to 55-60° C. and stirred at 55-60° C. for 10 min. The batch was cooled to room temperature and then to 0-5° C. The mixture was stirred at 0-5° C. for 1.5 hours, filtered, and the solid product was rinsed with cold IPA (1 mL) and dried. 0.369 g of oxycodone HCl (as Lot 2418-047) was obtained (3 ppm 14-hydroxycodeinone by LC/MS; 99.08A % pure by HPLC).

After two days of hydrogenation, the rest of the mixture was filtered to remove catalyst. The filtered mixture was distilled to minimize the solvents (DCM/IPA). The mixture was diluted with 1.5 mL of IPA, 0.5 mL of water and 0.13 g of 37% hydrochloric acid (1.32 mmol), and stirred at ambient temperature. The mixture was then heated to 55-60° C. and stirred at 55-60° C. for 10 min. The mixture was cooled to room temperature and then to 0-5° C. The mixture was stirred at 0-5° C. for 1.5 hours, filtered, and the solid product was rinsed with cold IPA (1.5 mL×2) and dried. 0.461 g of oxycodone HCl (as Lot 2418-051) was obtained (2 ppm 14-hydroxycodeinone by LC/MS; 98.66A % pure by HPLC).

Example 13

Hot Acid Stress Test of Oxycodone Hydrochloride from Example 11

To a 10 mL flask are charged 0.232 g (0.659) of low ABUK oxycodone HCl (T-zero: 2.5 ppm 14-hydroxycodeinone) and 5 mL of water. The mixture is stirred at room temperature to form a solution. 0.26 g of 3N aq. HCl (0.659 mmole, 1 molar equivalent) is then added. The batch is heated to 65° C. and monitored over 24 hours with LC/MS analysis. LC/MS analysis showed 4.2 ppm 14-hydroxycodeinone after 5 h and 6.1 ppm after 24 h. The slow growth over 24 was ascribed to degradation of unknown species other than 8α,14-dihydroxy-7,8-dihydrocodeinone.

| Entry | Hours in Hot Acid | ABUK (ppm) |
|---|---|---|
| 1 | 0 | 2.5 |
| 2 | 2 | 3.6 |
| 3 | 5 | 4.2 |
| 4 | 24 | 6.1 |

Example 14

Dry Heat Stress Test of Oxycodone Hydrochloride from Example 11

A 0.0225 g (0.597 sample of low ABUK oxycodone HCl (T-zero: 3.9 ppm 14-hydroxycodeinone) was placed in a standard lab drying oven under air at 62° C. and the level of 14-hydroxycodeinone was monitored by LC/MS for 14 days. No growth in the level of 14-hydroxycodeinone was observed.

| Entry | Days (at 62° C.) | ABUK (ppm) |
|---|---|---|
| 1 | T-zero | 3.9 ppm |
| 2 | 4 | 3.7 ppm |
| 3 | 7 | 4.0 ppm |
| 4 | 14 | 3.7 ppm |

Example 15

Hot Acid Stress Test of Oxycodone Base from Example 9

To a 10 mL flask are charged 0.20 g (0.634) of low ABUK oxycodone base (T-zero: 2.7 ppm 14-hydroxycodeinone by LC/MS) and 5 mL of water. The mixture is stirred at room temperature to form a solution. 0.26 g of 3N aq. HCl (0.659 mmole) is then added. The batch is heated to 65° C. and monitored over 24 hours with LC/MS analysis. LC/MS analysis showed 3.3 ppm 14-hydroxycodeinone after 5 h and 6.4 ppm after 24 h. The slow growth after 24 h was ascribed to degradation of unknown species other than 8α,14-dihydroxy-7,8-dihydrocodeinone.

| Entry | Hours in Hot Acid | ABUK (ppm) |
|---|---|---|
| 1 | 0 (r.t.) | 2.5 |
| 2 | 2 | 2.5 |
| 3 | 5 | 3.3 |
| 4 | 24 | 6.4 |

Example 16

Dry Heat Stress Test of Oxycodone Base from Example 9

A 0.0225 g (0.597 sample of low ABUK oxycodone (T zero: 3.3 ppm 14-hydroxycodeinone by LC/MS was placed in a standard lab drying oven under air at 62° C. and the level of 14-hydroxycodeinone was monitored by LC/MS for 14 days. No growth in the level of 14-hydroxycodeinone was observed

| Entry | Days (at 62° C.) | ABUK (ppm) |
|---|---|---|
| 1 | T-zero | 3.3 ppm |
| 2 | 4 | 3.4 ppm |
| 3 | 7 | 3.3 ppm |
| 4 | 14 | 3.6 ppm |

Analytical Method for PPM Level 14-Hydroxycodeinone and for 8α,14-dihydroxy-7,8-dihydrocodeinone and 8β,14-dihydroxy-7,8-dihydrocodeinone (HPLC/MS-SIM)

1.1 Reagents and Materials:

(Equivalent Reagents and Materials may be Substituted)

| | |
|---|---|
| Methanol (MeOH) | Fisher Scientific, HPLC Grade |
| Acetonitrile (ACN) | Fisher Scientific, HPLC Grade |
| Ammonium Acetate (NH$_4$OAc) | J. T. Baker, HPLC Grade |
| Purified Water (H$_2$O) | MilliQ, Model A10 Gradient Water System |
| 14-Hydroxy Codeinone | JM Qualified Reference Standard |
| 7,8-Dihydro-8β-14-Dihydroxycodeinone (Inert β-Diol) | Retention Time Marker (not qualified) |

1.2 Instrumentation:

(Equivalent Instrumentation can be used)

| | |
|---|---|
| HPLC | Waters Acquity UPLC System |
| UV Detector | Waters Acquity PDA Detector |
| Mass Spec | Waters Q-Tof Premier |
| Data System | Waters MassLynx 4.1 |
| Balance | Mettler-Toledo, Model AT261 or PG503-S, Delta Range |

1.3 Mobile Phase Preparation:

(For 1 L Each)

Mobile Phase A: Weigh~0.77 (±0.03) g of Ammonium Acetate into a suitable mobile phase bottle, dissolve with 950 mL of deionized water, add 25 mL of Acetonitrile and 25 mL of MeOH to the container. Mix well and degas.

Mobile Phase B: Weigh~0.77 (±0.03) g of Ammonium Acetate into a suitable mobile phase bottle, dissolve with 100 mL of deionized water, add 450 mL of Acetonitrile and 450 mL of MeOH to the container. Mix well and degas.

The diluent: MeOH (free base) or 0.2% (v/v) TFA/H$_2$O (HCl salt).

1.4 Operating Conditions:

| | |
|---|---|
| Column | Waters, XBridge, Phenyl, 5 μm, 4.6 × 150 mm |
| Col. Temperature | Ambient |
| Sample Temp | Ambient |
| Injection Volume | 10 μL |
| Detection | UV at 220 nm |
| Flow Rate | 0.8 mL/min, with a splitter to lead ~0.2 mL/min to the mass spec. |
| Analysis Time | 30 min |
| Run Time | 35 min |

| Linear Gradient (Mixing) Conditions: | Time (min) | % MP A | % MP B | Curve |
|---|---|---|---|---|
| | initial | 100 | 0 | 6 |
| | 22 | 73 | 27 | 6 |
| | 25 | 10 | 90 | 6 |
| | 30 | 10 | 90 | 6 |
| | 31 | 100 | 0 | 6 |
| | 40 | 100 | 0 | 6 |

Mass Spec Parameters:

| Source | | Instrument | | Acquisition | |
|---|---|---|---|---|---|
| Capillary | 0.5 (diols) 1.5 (ABUK) | LM Resol | 4.7 | Source | ESI |
| Spl Cone | 30 | HM Resol | 15.0 | | |
| Extra Cone | 5.0 | Ion Energy | 0.0 | Source | ESI |
| Ion Guide | 3.5 | Pre-filter | 5.0 | Polarity | + |
| Source Temp | 120 | Collision Energy | 5.0 | Analyzer Mode | V |
| Cone Gas | 0 | Cell Entrance | 2.0 | Sensitivity | Maximum at 332 a.u. (Diols) Maximum at 314 a.u. (ABUK) |
| Desolvation Temp | 450 | Cell Exit | −10.0 | Scan Scan Delay | 0.3 0.02 |
| Detector Voltage | 1920 | Collision Cell | 0.4 | Data Format | Continuum |
| Desolvation | 700 | Ion Guide | 0.0 | Mass Range | 332.0-332.3 a.u. (Diols) 313.9-314.3 a.u. (ABUK) |

1.5 Approximate Retention Times of Known Analytes:

| Analyte | Approximate Retention Time* (min) | RRT |
|---|---|---|
| α-Diol | 15.8 | 0.82 |
| β-Diol | 17.7 | 0.91 |
| Oxycodone | 19.5** | 1.00 |
| 14-Hydroxy Codeinone | 23.0 | 1.18 |

*The retention time is extremely sensitive to the mobile phase.
**The peak is saturated.

1.6 Impurity Working Standard Solution Preparation

Weigh 15 mg (±20%, accurate to the second digit passed the decimal point) each of 14-Hydroxy Codeinone reference standard and β-Diol into a 100 mL volumetric flask. Dissolve and then dilute to the volume with MeOH. Sonicate for 30 sec and mix well. This is the impurity stock solution.

Transfer 2.0 mL of the impurity stock solution into a 100 mL volumetric flask, dilute to volume with 0.2% TFA/ $H_2O$, and mix well. This is the impurity stock solution-2.

Transfer 5.0 mL of the impurity stock solution-2 into a 100 mL volumetric flask, dilute to volume with 0.2% TFA/ $H_2O$, and mix well. This is the impurity working standard solution.

1.7 Resolution Solution Preparation:

Accurately weigh 150 mg (±10 mg) of the Oxycodone material, which has the lowest possible level of β-Diol, into a 10 mL volumetric flask. Dissolve and dilute to volume with the impurity stock solution-2 (Sonication may be necessary).

1.8 Sample Solution Preparation:

In duplicate, accurately weigh 150 mg (±10 mg) of the sample into a 10 mL volumetric flask. Dissolve the sample and dilute to volume with the diluent (Sonication may be necessary).

1.9 System Equilibration and Conditioning:

Pump Mobile Phase A through the column for at least 20 minutes followed by pump Mobile Phase B for at least another 20 minutes at a flow rate of 0.8 mL/min. Switch to Initial assay conditions and pump for at least 20 minutes.

1.10 Procedure:

Separately inject the diluent as a blank.
Inject the resolution solution once.
Inject the impurity working standard three times.
Inject each sample solution under the full gradient.
Inject the diluent at the end.
Quantify the level of 14-Hydroxy Codeinone in the sample by comparing to the averaged corresponding peak specific response (SR) of the standard solution.
Report the level of 14-Hydroxy Codeinone found in the sample to the nearest 0.0001%.
Report the peak area of the diols for information only.

1.11 System Suitability:

The RRT of the inert diol (MS signal) relevant to the saturated Oxycodone (UV signal) is NMT 0.95.

1.12 Calculations:

1.12.1 ABUK % w/w (in free base form):

$$\% \text{ w/w} = \frac{(ABUK \text{ in Sample}^{Avg\ PA})(100)(ABUK \text{ Std}^{Conc.mg/mL})}{(ABUK \text{ Std Purity}\{\text{in decimal}\})}$$
$$\frac{}{(ABUK \text{ Std}^{Avg\ PA})(\text{Sample}^{Conc.mg/mL}) \times CF}$$

Where: $PA$ = Peak Area

Std = Standard

Conversion Factor $(CF) = \frac{\text{MW of the base form}}{\text{MW of HCl Salt form}}$ PPM = % w/w × 1000000

1.13 Typical Chromatograms:

Figure 1:
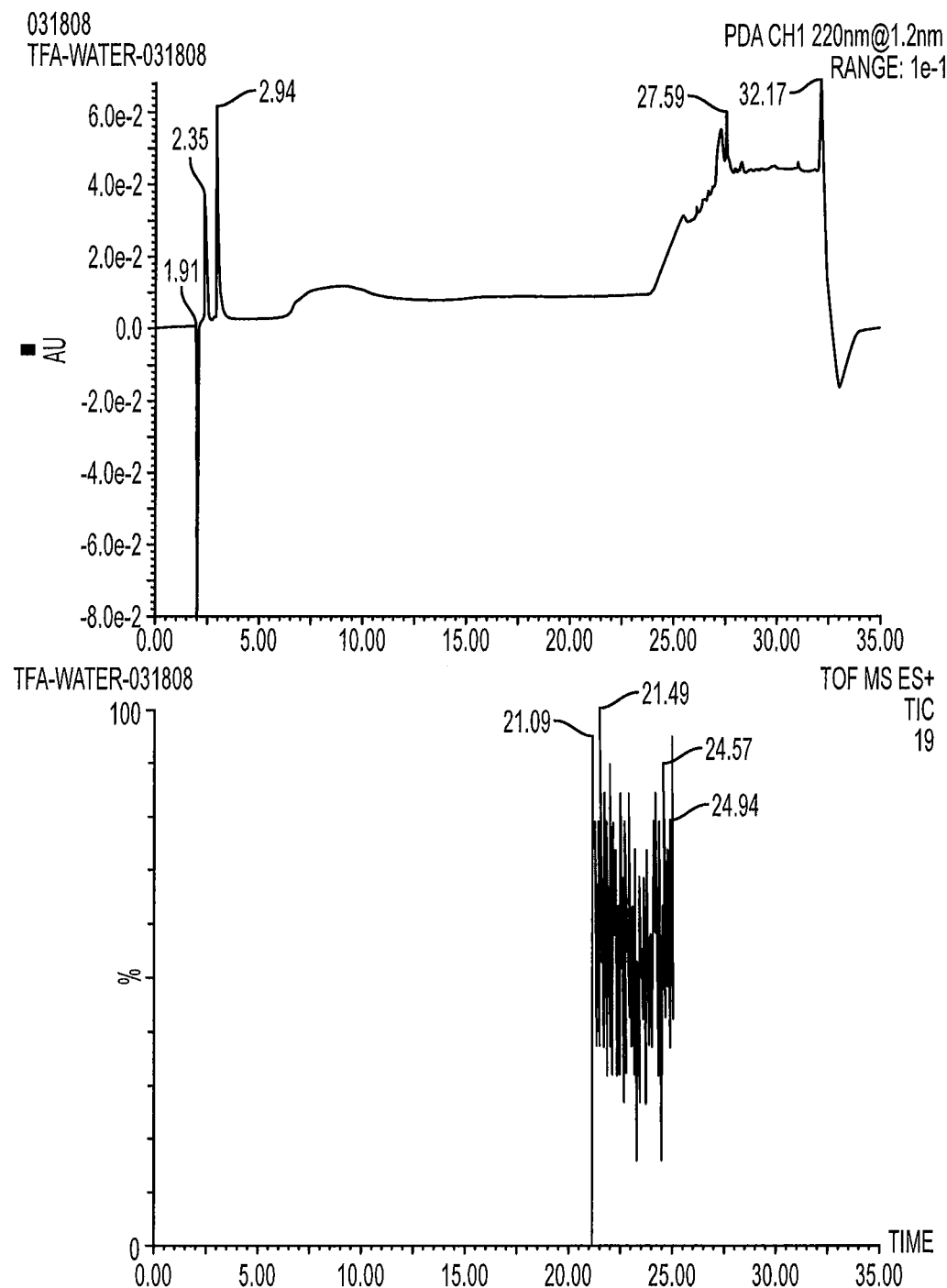
FIG. 1 shows a typical chromatogram using 0.2% TFA/ $H_2O$ as Blank.
Figure 2:
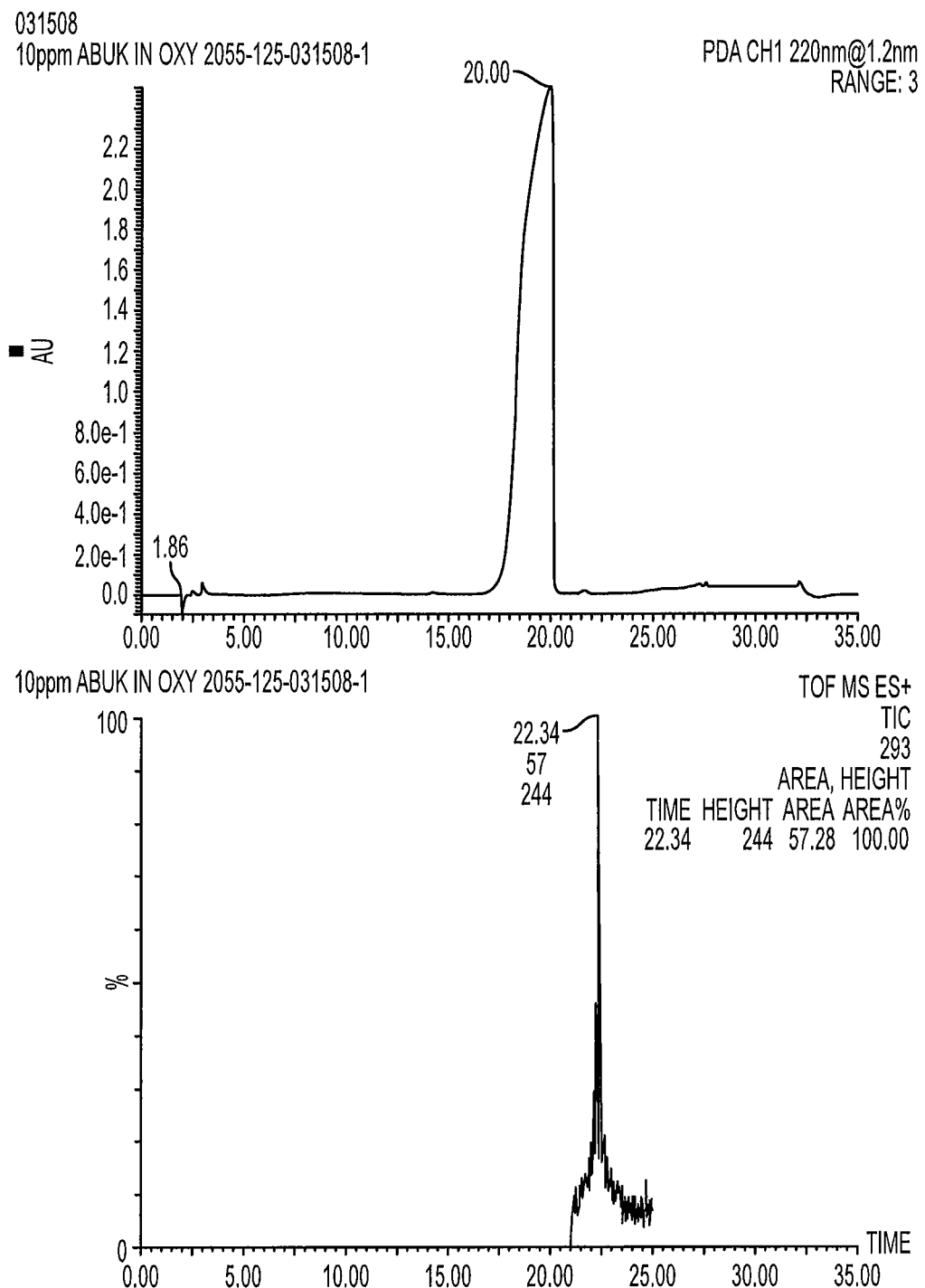
FIG. 2 shows a typical chromatogram using a Resolution Solution (10 PPM ABUK Spiked)
Figure 3:
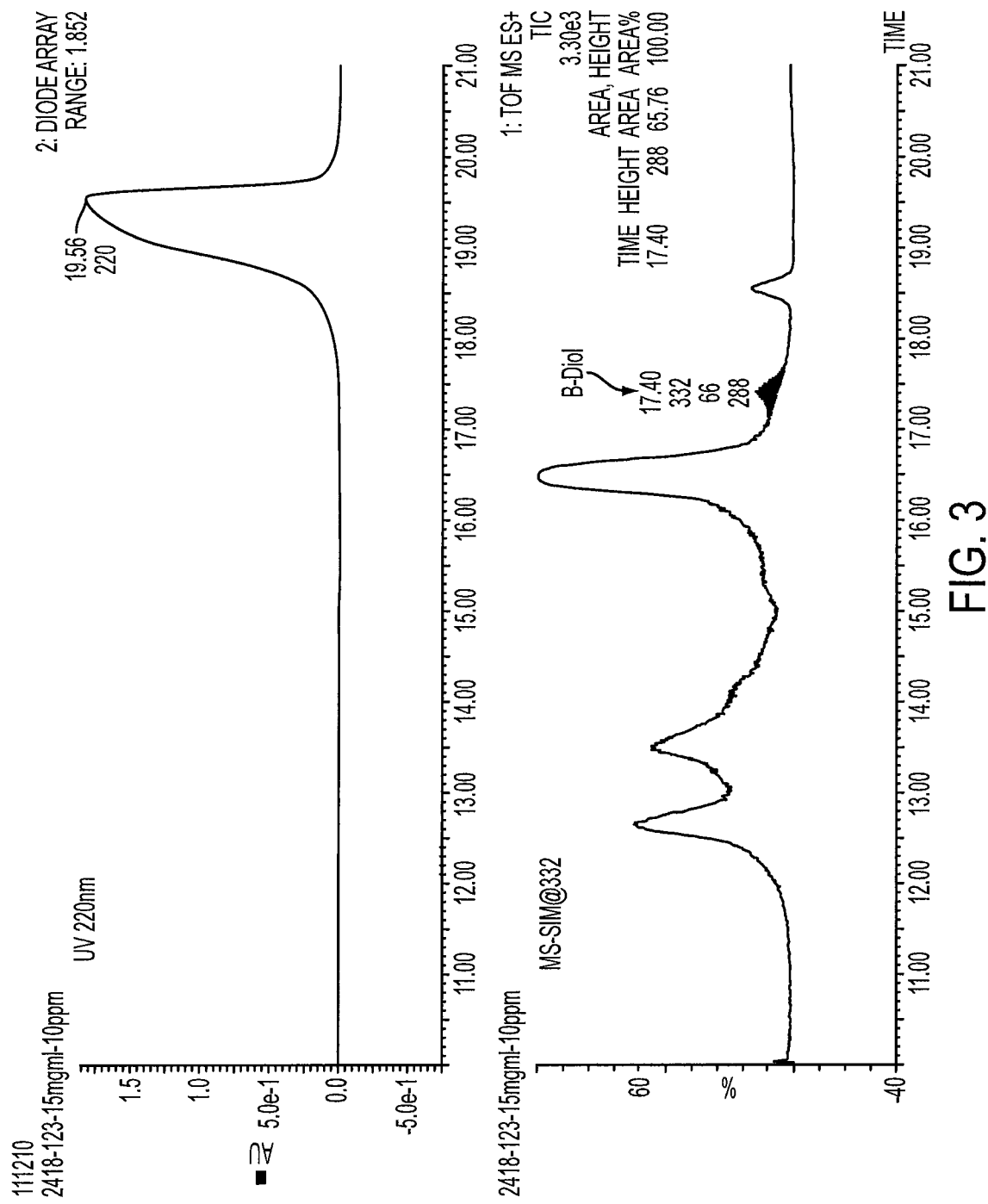
FIG. 3 shows a typical chromatogram using a Resolution Solution (10 PPM β-Diol Spiked)
Figure 4:
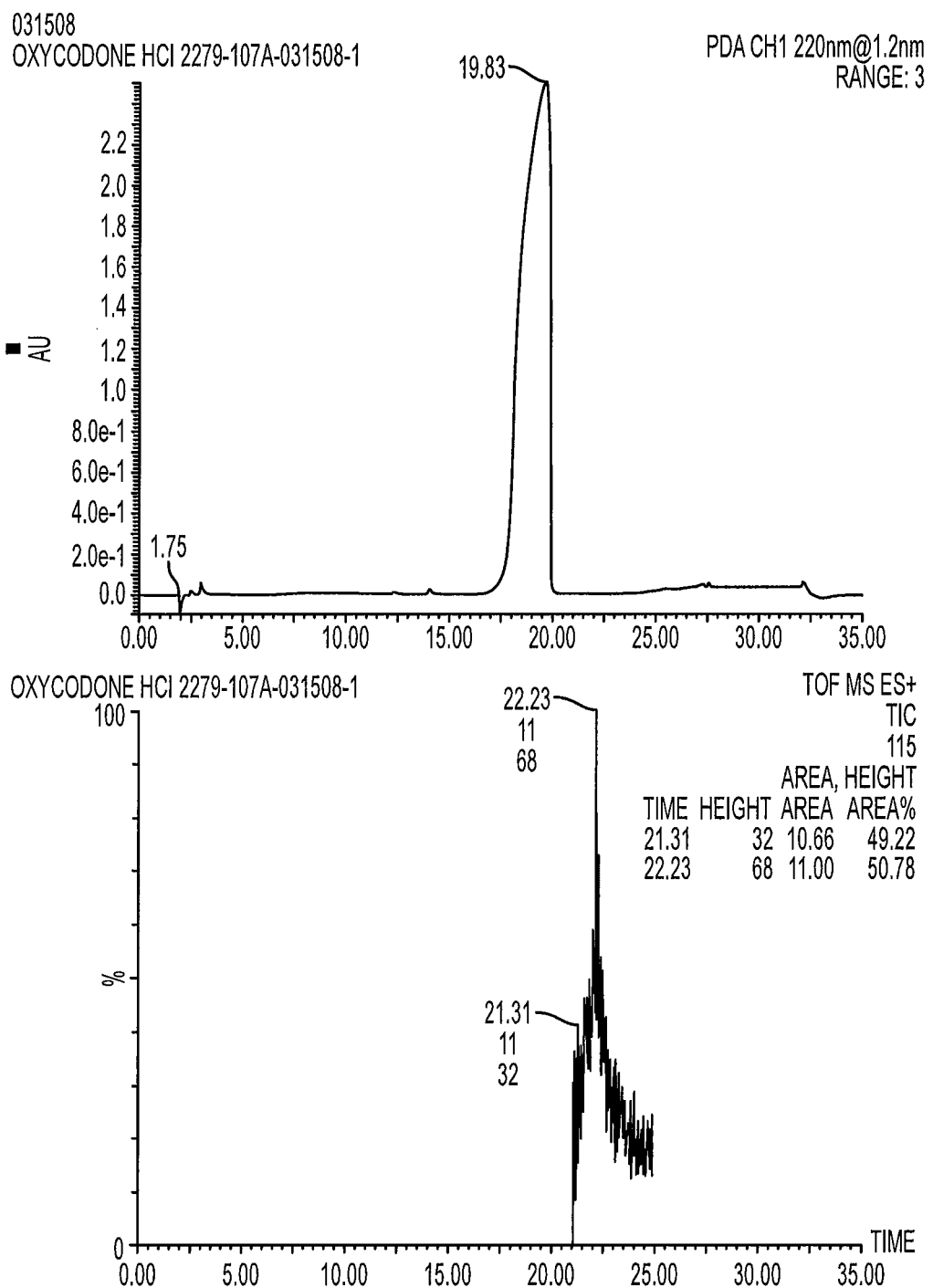
FIG. 4 shows a typical chromatogram using a Sample Solution (Containing ~3 PPM of 14-Hydroxy Codeinone)
Figure 5:
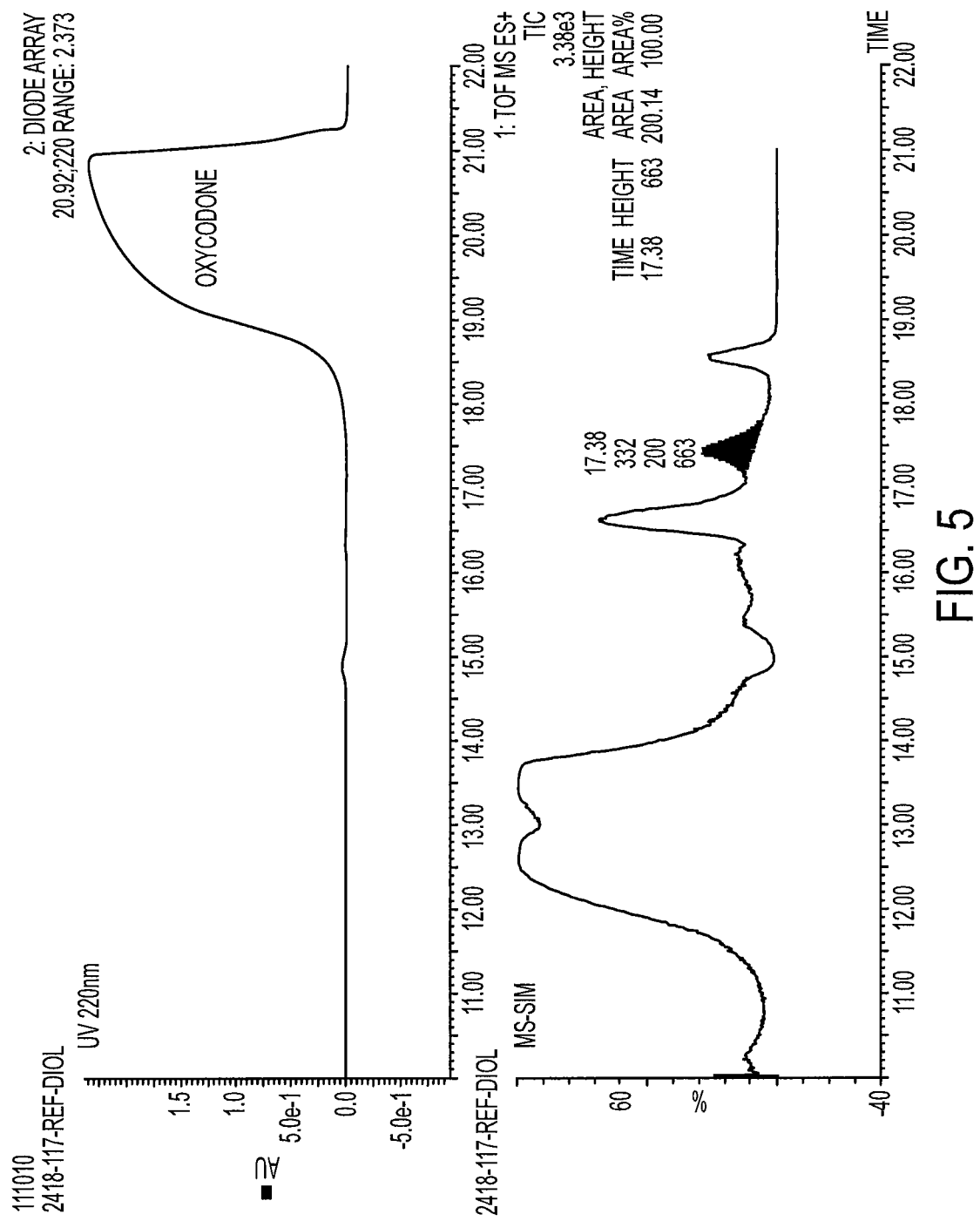
FIG. 5 shows a typical chromatogram using a Sample Solution (Containing ~30 PPM of β-Diol)

What is claimed:

1. A method of preparing oxycodone, comprising contacting 14-hydroxycodeine with a catalyst under conditions sufficient to cause rearrangement of the 14-hydroxycodeine to form oxycodone free base.

2. The method of claim 1, wherein the 14-hydroxycodeine is formed by reduction of 14-hydroxycodeinone.

3. The method of claim 2, wherein the 14-hydroxycodeinone is derived from thebaine.

4. The method of claim 1, further comprising purifying the oxycodone free base.

5. The method of claim 1, further comprising converting the oxycodone free base to an oxycodone salt.

6. The method of claim 3, wherein the 14-hydroxycodeinone contains at least one isomer of 8,14-dihydroxy-7,8-dihydrocodeinone as an impurity and wherein, during the reduction of 14-hydroxycodeinone to form 14-hydroxycodeine, the 8,14-dihydroxy-7,8-dihydrocodeinone is reduced to at least one isomer of 8,14-dihydroxy-7,8-dihydrocodein-6-ol.

7. The method of claim 6, wherein at least one isomer of 8,14-dihydroxy-7,8-dihydrocodeinone is formed during oxidation of thebaine.

8. The method of claim 6, wherein the at least one isomer of 8,14-dihydroxy-7,8-dihydrocodeinone is an alpha-isomer, a beta-isomer or both the alpha-isomer and the beta-isomer at the C-8 hydroxyl group.

9. The method of claim 2, wherein the reduction comprises use of a hydride reagent.

10. The method of claim 9, wherein the hydride reagent is selected from L-selectride, N-selectride and sodium borohydride.

11. The method of claim 2, wherein the reduction is performed in a solvent or a mixture of solvents.

12. The method of claim 11, where in the mixture of solvents comprises at least one alcohol and at least one aprotic organic solvent.

13. The method of claim 12, wherein the alcohol is selected from the group consisting of methanol, ethanol, isopropanol, n-propanol, isobutanol, n-butanol and 2-butanol.

14. The method of claim 12, where in the aprotic organic solvent is selected from the group consisting of methylene chloride, 1,2-dichloroethane, ethyl acetate, isopropyl acetate, tetrahydrofuran, toluene, xylene and methyl tert-butyl ether.

15. The method of claim 2, wherein less than 100 ppm of 14-hydroxycodeinone is present after the reduction.

16. The method of claim 2, wherein less than 50 ppm of 14-hydroxycodeinone is present after the reduction.

17. The method of claim 8, wherein less than 2 ppm of 8α,14-dihydroxy-7,8-dihydrocodeinone is present after the 14-hydroxycodeinone is reduced.

18. The method of claim 1, wherein the catalyst is a ligand-complexed metal catalyst.

19. The method of claim 18, wherein the ligand is a phosphine.

20. The method of claim 18, wherein the metal is rhodium or ruthenium.

21. The method of claim 20, wherein the catalyst is

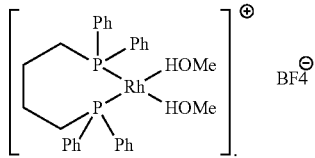

22. The method of claim 1, wherein the contacting is performed in a solvent or a mixture of solvents.

23. The method of claim 22, wherein the contacting is performed in said mixture of solvents and wherein the mixture of solvents comprises at least one alcohol and at least one aprotic organic solvent.

24. The method of claim 23, wherein the alcohol is selected from the group consisting of methanol, ethanol, isopropanol, n-propanol, isobutanol, n-butanol and 2-butanol.

25. The method of claim 23, where in the aprotic organic solvent is selected from the group consisting of methylene chloride, 1,2-dichloroethane, ethyl acetate, isopropyl acetate, tetrahydrofuran, toluene, xylene and methyl tert-butyl ether.

26. The method of claim 1, wherein the contacting is performed at a temperature in a range from about 25° C. to about 100° C.

27. The method of claim 4, wherein the purifying comprises contacting the oxycodone free base with a solution comprising sodium meta-bisulfite.

28. The method of claim 27, wherein the solution is a $Na_2S_2O_5/Na_2SO_3$ buffered solution.

29. The method of claim 5, wherein the oxycodone salt is oxycodone hydrochloride.

30. An oxycodone free base having less than 25 ppm 14-hydroxycodeinone and less than 2 ppm of 8α,14-dihydroxy-7,8-dihydrocodeinone, wherein the oxycodone free base is made by the method of claim 4.

31. The oxycodone free base of claim 30, wherein less than 10 ppm of 14-hydroxycodeinone is present.

32. The oxycodone free base of claim 30, wherein less than 5 ppm of 14-hydroxycodeinone is present.

33. An oxycodone free base made by the method of claim 27.

34. The method of claim 4, wherein the purifying comprises contacting the oxycodone free base with a mixture comprising an alcohol, a palladium on carbon catalyst, and hydrogen, and optionally a chlorinated solvent.

35. The method of claim 34, wherein the alcohol comprises at least one of methanol, isopropanol, ethanol, and butanol.

36. The method of claim 34, wherein the chlorinated solvent is dichloromethane, dichloroethane, chloroform, or chlorobenzene.

37. The method of claim 34, wherein the palladium on carbon catalyst is 5% or 10% by weight of palladium on carbon.

38. The method of claim 34, wherein the hydrogen is pressurized from about 15 psi to about 50 psi.

39. The method of claim 34, wherein the contacting is performed at a temperature from about 18° C. to about 35° C.

40. The method of claim 34, wherein the oxycodone free base is isolated as a solid.

41. The method of claim 40, wherein the solid contains less than 10 ppm 8α,14-dihydroxy-7,8-dihydrocodeinone.

42. The method of claim 41, wherein less than 2 ppm of 8α,14-dihydroxy-7,8-dihydrocodeinone is present.

43. The method of claim 40, wherein the solid contains less than 10 ppm 14-hydroxycodeinone.

44. The method of claim 40, where in the solid contains less than 2 ppm 14-hydroxycodeinone.

45. The method of claim 34, wherein the oxycodone free base is converted to oxycodone hydrochloride salt and the salt is isolated as a solid.

46. The method of claim 45, wherein the oxycodone free base is not isolated as a solid prior to said converting.

47. The method of claim 46, wherein the oxycodone hydrochloride salt contains less than 5 ppm 14-hydroxycodeinone.

48. The method of claim 40, wherein the solid oxycodone free base is contacted with ethanol.

49. The method of claim 48, wherein the contacting is performed at an elevated temperature.

50. The method of claim 48, wherein the oxycodone free base is re-isolated after the contacting with ethanol.

51. The method of claim 50, wherein the re-isolated oxycodone free base contains less than 5 ppm 8α,14-dihydroxy-7,8-dihydrocodeinone.

52. The method of claim 51, wherein less than 2 ppm of 8α,14-dihydroxy-7,8-dihydrocodeinone is present.

53. The method of claim 50, wherein the re-isolated oxycodone free base contains less than 5 ppm 14-hydroxycodeinone.

54. An oxycodone free base made by the method of claim 34 comprising less than 2 ppm of 8α,14-dihydroxy-7,8-dihydrocodeinone and less than 5 ppm 14-hydroxycodeinone.

55. An oxycodone free base made by the method of claim 48 comprising less than 2 ppm of 8α,14-dihydroxy-7,8-dihydrocodeinone and less than 5 ppm 14-hydroxycodeinone.

56. An oxycodone hydrochloride made by the method of claim 5 having less than 25 ppm 14-hydroxycodeinone and less than 2 ppm of 8α,14-dihydroxy-7,8-dihydrocodeinone.

57. The oxycodone hydrochloride of claim 56 having less than 10 ppm 14-hydroxycodeinone.

58. The oxycodone hydrochloride of claim 56 having less than 5 ppm 14-hydroxycodeinone.

59. The oxycodone hydrochloride of claim 56, wherein less than 2 ppm of 14-hydroxycodeinone is present.

60. The oxycodone free base of claim 33, wherein less than 2 ppm of 8α,14-dihydroxy-7,8-dihydrocodeinone is present.

* * * * *